United States Patent
Joy et al.

(10) Patent No.: US 10,336,923 B2
(45) Date of Patent: Jul. 2, 2019

(54) PHOTORESPONSIVE POLYMERS FOR ADHESIVE APPLICATIONS

(71) Applicants: Abraham Joy, Copley, OH (US); Ali Dhinojwala, Akron, OH (US); Kaushik Mishra, Akron, OH (US)

(72) Inventors: Abraham Joy, Copley, OH (US); Ali Dhinojwala, Akron, OH (US); Kaushik Mishra, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 15/311,319

(22) PCT Filed: May 15, 2015

(86) PCT No.: PCT/US2015/031126
§ 371 (c)(1),
(2) Date: Nov. 15, 2016

(87) PCT Pub. No.: WO2015/175963
PCT Pub. Date: Nov. 19, 2015

(65) Prior Publication Data
US 2017/0081568 A1 Mar. 23, 2017

Related U.S. Application Data

(60) Provisional application No. 61/993,654, filed on May 15, 2014.

(51) Int. Cl.
| | | |
|---|---|---|
| *C08F 2/46* | (2006.01) | |
| *C08F 2/50* | (2006.01) | |
| *C08G 61/04* | (2006.01) | |
| *C09J 133/08* | (2006.01) | |
| *C09B 57/02* | (2006.01) | |
| *G03F 7/039* | (2006.01) | |
| *C09B 69/10* | (2006.01) | |
| *A61F 13/02* | (2006.01) | |
| *A61L 15/24* | (2006.01) | |
| *A61L 15/58* | (2006.01) | |
| *B32B 27/06* | (2006.01) | |
| *C09J 7/02* | (2006.01) | |

(52) U.S. Cl.
CPC .......... *C09J 133/08* (2013.01); *A61F 13/0253* (2013.01); *A61L 15/24* (2013.01); *A61L 15/58* (2013.01); *B32B 27/06* (2013.01); *C09B 57/02* (2013.01); *C09B 69/109* (2013.01); *C09J 7/0217* (2013.01); *G03F 7/039* (2013.01); *B32B 2307/41* (2013.01); *B32B 2307/412* (2013.01); *B32B 2535/00* (2013.01)

(58) Field of Classification Search
CPC .......... C09J 133/08; A61L 15/58; A61L 15/24; B32B 2307/412; B32B 2307/41; B32B 27/06; B32B 2535/00; C09B 57/02; C09B 69/109; A61F 13/0253; G03F 7/039
USPC ................................................. 522/1; 520/1
See application file for complete search history.

(56) References Cited

U.S. PATENT DOCUMENTS

| | | | |
|---|---|---|---|
| 4,391,687 A | 7/1983 | Vesley | |
| 6,184,264 B1 * | 2/2001 | Webster | A61F 13/0203 156/272.2 |
| 8,053,151 B2 | 11/2011 | Wu et al. | |
| 8,415,432 B1 | 4/2013 | Mruk et al. | |
| 2003/0105258 A1 | 6/2003 | Husemann et al. | |
| 2003/0152623 A1 * | 8/2003 | Bromberg | A61K 8/042 424/468 |
| 2007/0299231 A1 * | 12/2007 | Doehler | C08G 77/08 528/29 |
| 2008/0199804 A1 * | 8/2008 | Oohashi | B41C 1/1008 430/270.1 |
| 2009/0023085 A1 | 1/2009 | Tsuchimura | |
| 2009/0216170 A1 * | 8/2009 | Robinson | A61F 13/0203 602/60 |
| 2011/0224593 A1 * | 9/2011 | Tunius | A61L 15/585 602/54 |
| 2015/0210805 A1 * | 7/2015 | Harth | C08G 65/34 526/273 |
| 2016/0206743 A1 * | 7/2016 | Harth | C08G 65/3326 |

FOREIGN PATENT DOCUMENTS

| | | | | |
|---|---|---|---|---|
| CN | 103204837 | * | 7/2013 | |
| WO | 9706836 A2 | | 2/1997 | |
| WO | 02092712 A1 | | 11/2002 | |
| WO | 2013090892 A1 | | 6/2013 | |
| WO | WO-2013090892 A1 | * | 6/2013 | ............. C08G 63/06 |

OTHER PUBLICATIONS

Wang et al, CN 103204837 Machine Translation, Jul. 17, 2013 (Year: 2013).*

Kim. et al., Photo-responsive bio-inspired adhesives: facil control of adhesion strength via a photcleavable crosslinker, Polym. Chem. 8, 6300 (2017).

\* cited by examiner

*Primary Examiner* — Jessica Whiteley
(74) *Attorney, Agent, or Firm* — Renner Kenner Greive Bobak Taylor and Weber

(57) ABSTRACT

Provided is a pressure sensitive adhesive polymer comprising adhesive polymerscrosslinked with a crosslinker that includes a photoresponsive group. Also provided is a method for preparing a pressure sensitive adhesive polymer comprising: polymerizing an vinyl monomer and photoresponsive crosslinker with two acryl end groups.

9 Claims, 3 Drawing Sheets

PHOTORESPONSIVE POLYMERS FOR ADHESIVE APPLICATIONS

CROSS-REFERENCE TO RELATED APPLICATIONS

The present application claims priority to U.S. Provisional Patent Application No. 61/993,654, filed May 15, 2014, incorporated herein by reference.

FIELD OF THE INVENTION

One or more embodiments of are directed to adhesive polymers crosslinked with a crosslinker that includes a photoresponsive group.

BACKGROUND OF THE INVENTION

Adhesives may be broadly divided in two classes: structural and pressure-sensitive. To form a permanent bond, structural adhesives harden via processes such as evaporation of solvent, reaction with UV radiation (as in dental adhesives), chemical reaction (such as multi part epoxy), or cooling (as in hot melt). In contrast, pressure-sensitive adhesives form a bond simply by the application of light pressure to marry the adhesive with the adherend. Pressure-sensitive adhesives are designed with a balance between flow and resistance to flow. The bond forms because the adhesive is soft enough to flow, or wet the adherend. The bond has strength because the adhesive is hard enough to resist flow when stress is applied to the bond. Once the adhesive and the adherend are in proximity, there are also molecular interactions such as van der Waals forces involved in the bond, which contribute significantly to the ultimate bond strength. PSAs exhibit viscoelastic (viscous and elastic) properties, both of which are used for proper bonding.

As the name suggests, pressure-sensitive adhesives are capable of bonding to surfaces simply by the application of light pressure. This makes them very convenient products and accounts for its usage in fields as varied as automotive, electronics and dental applications. Acrylic polymers have been most widely used as pressure-sensitive adhesives in commercial products because of the low-cost, nontoxicity, transparency, and good resistance to weathering.

Most conventional pressure-sensitive adhesives are designed for applications at room temperature and with multiple-components. However, the demand for single-component acrylic pressure-sensitive adhesives with high adhesive properties applicable at wide ranges of temperature has increased rapidly in recent years. It is well-known that tack (the ability of pressure-sensitive adhesives to be quickly adhered to an objective surface at a slight pressure), peel strength (the ability of pressure-sensitive adhesives to resist interface separation by peeling), and shear strength (the ability of pressure-sensitive adhesives to resist creep when shear force is applied up on) are the major parameters that define the end-use properties of pressure-sensitive adhesives. The values of these parameters are associated with and can be adjusted by intrinsic viscosity, glass transition temperature (Tg), molecular weight (Mw), and crosslinking density. Generally, modulating the crosslinking density is the most effective method to improve adhesive properties, especially for heat and chemical resistance. While those skilled in the art generally recognize that properties of pressure-sensitive adhesives can be adjusted, hese adjustments generally produce static results. Presently there is a need in the art for pressure-sensitive adhesives with controllable properties such as adhesive strength.

SUMMARY OF THE INVENTION

One or more embodiments provides a photoresponsive adhesive polymer comprising adhesive polymers crosslinked with a crosslinker that includes a photoresponsive group.

Other embodiments provide a method for preparing a photoresponsive adhesive polymer comprising: polymerizing a vinyl monomer and photoresponsive crosslinker with two acryl end groups.

Other embodiments provide a medical dressing comprising: a transparent or partially transparent backing layer with a first and a second side; and a photoresponsive adhesive polymer comprising crosslinked adhesive polymers with a crosslinker that includes a photoresponsive group coated on the first side of the backing layer.

DETAILED DESCRIPTION OF ILLUSTRATIVE EMBODIMENTS

Figure 1:
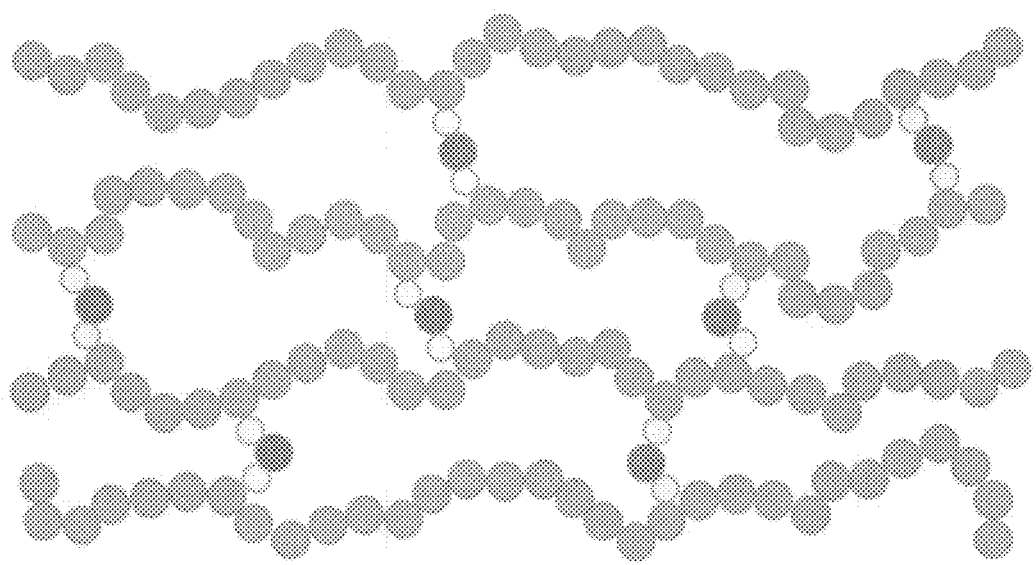
FIG. 1 represents photoresponsive moieties as part of both the main chain and crosslinkers for the crosslinked adhesive system. On irradiation with the specific wavelength corresponding to the photoresponsive group the chains fall apart and thus lose their physical strength.
Figure 1:
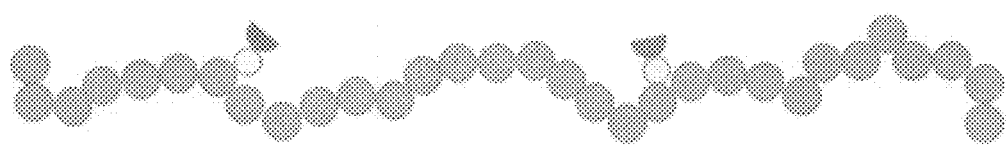
Figure 2:
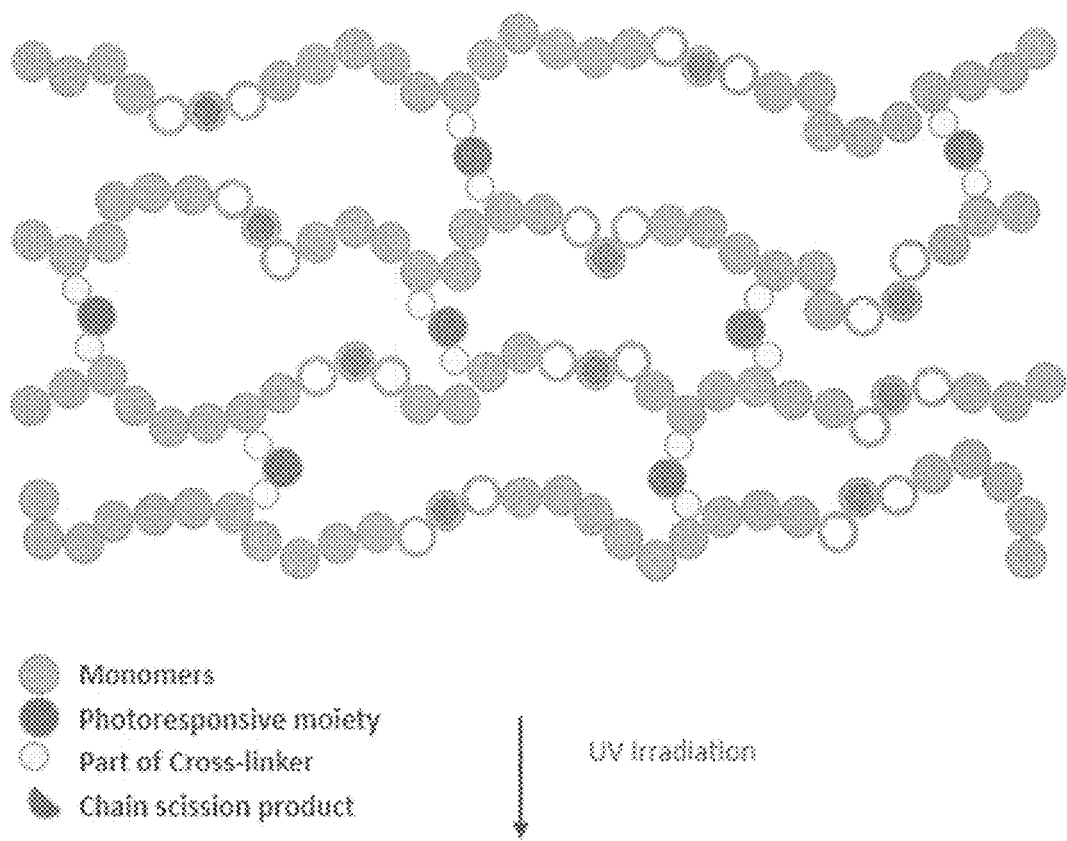
FIG. 2 represents photoresponsive moieties as part of the crosslinkers for the crosslinked adhesive system. On irradiation with the specific wavelength corresponding to the photoresponsive group the chains fall apart and thus lose their physical strength.
Figure 3:
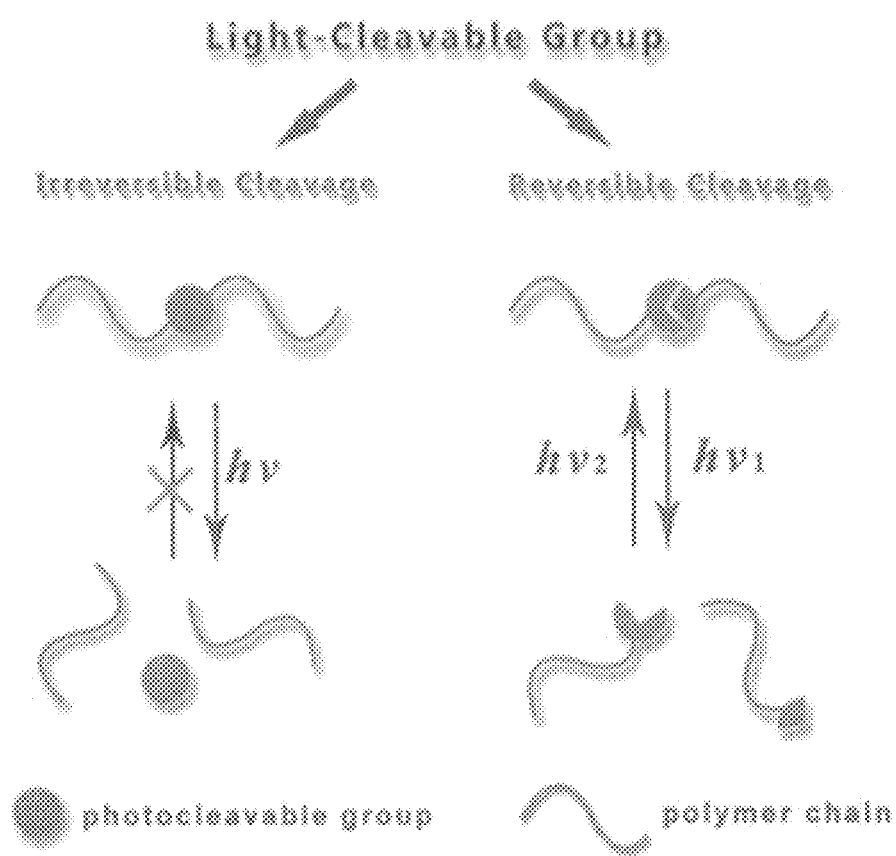
FIG. 3 proveds a scheme displaying light cleavable groups (Photoresponsive groups) including irreversible and reversible systems as shown in the figure. In certain embodiments, irreversible cleavage as shown on the left is may be performed with an alkoxyphenacyl group and the reversible cleavage, as shown on the right may be performed with a coumarin group.

Embodiments are based, at least in part, on the discovery that photoresponsive groups may be used in a crosslinker of an adhesive polymer to produce a switchable adhesive. The photoresponsive groups of the switchable adhesive may be reversibly crosslinked to control the strength of the adhesive. For the purpose of this disclosure, a switchable polymer that includes a photoresponsive group placed in a crosslinker of an adhesive polymer may simply be referred to as a photoresponsive adhesive. By varying polymerization techniques and the molecular weight, photoresponsive adhesives may be used as water-based adhesives, solvent based adhesives, or hot melt adhesives. Due to the ability to control the strength of the photoresponsive adhesives, the photoresponsive adhesive may be suitable for use as an adhesive in a medical dressing.

Advantageously, the photoresponsive adhesive may be used as a single-component adhesive. Single-component adhesives are advantageous because they include a built in crosslinker. Generally, single-component adhesives are more convenient than multi-component adhesives, because adhesive and crosslinker of a multi-component adhesives must be stored separately. Additionally, quality control issues may arise from poorly mixed multi-component adhesives or multi-component adhesives that use incorrect ratios of components.

In one or more embodiments, the pressure sensitive adhesive polymer comprises adhesive polymers crosslinked with a crosslinker that includes a photoresponsive group. Suitable adhesive polymers include those that are capable of being crosslinked and adhere to an objective surface with pressure. In one or more embodiments, the photoresponsive group in not pendantly attached to the crosslinker. In these or other embodiments, the photoresponsive group is connected to the crosslinker by at least two bonds.

In one or more embodiments, the photoresponsive adhesive may have a high adhesive strength conformation and a low adhesive strength conformation. In one or more embodiments, the high adhesive conformation is where the photoresponsive adhesive is crosslinked and in the low adhesive conformation the crosslinks are broken. The strength of the may be measured by a peel test. In one or more embodiments the high strength conformation is at least 2 times stronger, in other embodiments at least 3 times stronger, in other embodiments at least 4 times stronger, and in still other embodiments at least 5 times stronger than the low strength conformation. In one or more embodiments, the high strength conformation is at most 100 times stronger, in other embodiments at most 50 times stronger, in other embodiments at most 20 times stronger, and in still other embodiments at most 10 times stronger than the low strength conformation. In these or other embodiments, the high strength conformation from about 2 times to about 100 times stronger, in other embodiments from about 3 times to about 50 times stronger, in other embodiments from about 4 times to about 20 times stronger, and in still other embodiments from about 5 times to about 10 times stronger than the low strength conformation.

Suitable photoresponsive groups includes groups that may reversibly form dimers or photocleave when exposed to light. Specific examples of photoresponsive include coumarin groups and alkoxyphenacyl groups.

In one or more embodiments, the photoresponsive group may be a coumarin group. Those skilled in the art will appreciate that a coumarin group may be defined by the following formula:

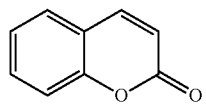 [SMILES: O=c1ccc2ccccc2o1]

In one or more embodiments, the photoactive coumarin group may have a substitution at any of the hydrogen atoms of the base coumarin group. In these or other embodiments, the coumarin group may have one or more hydrogen atoms substituted with a bromine atom, an iodine atom, or an alkoxy group.

Coumarin groups are useful in the production of photoresponsive adhesives because they can be used to provide a reversible crosslink. Coumarin groups are capable of undergoing photodimerization with another coumarin group or when the photoresponsive adhesive is irradiated with light. In one or more embodiments, photoresponsive adhesives with a coumarin group undergo photodimerization when irradiated at a wavelength of about 320 nm to about 420 nm. The dimerization may be reversed by the irradiation of a crosslinked polymer. In one or more embodiments, the dimer of coumarin group may separate when irradiated at a wavelength of about 230 nm to about 300 nm.

In one or more embodiments, the photoresponsive group may be a alkoxyphenacyl group. Those skilled in the art will appreciate that a alkoxyphenacyl group may be defined by the following formula:

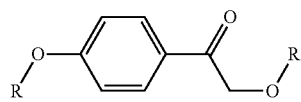

where each R is individually an organic group.

In one or more embodiments, the alkoxyphenacyl group may have a substitution at any of the hydrogen atoms of the base alkoxyphenacyl group. In these or other embodiments, the alkoxyphenacyl group may have one or more hydrogen atoms substituted with a bromine atom, an iodine atom, or an alkoxy group.

Alkoxyphenacyl groups are useful in the production of photoresponsive adhesives because they can be used to provide a photocleaveable bond. Alkoxyphenacyl groups are capable of undergoing photocleaveage when the photoresponsive adhesive is irradiated with light. In one or more embodiments, photoresponsive adhesives with an alkoxyphenacyl group undergo photocleaveage when irradiated at a wavelength of about 250 nm to about 350 nm.

In one or more embodiments, the pressure sensitive adhesive polymer may be prepared by polymerizing a vinyl monomer and photoresponsive crosslinker with two acryl end groups. As those skilled in the art will appreciate, an acryl end group may be defined by the following formula

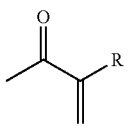

where R is a hydrogen atom or an akyl group.

In one or more embodiments, the photoresponsive adhesive may be polymerized through conventional radical polymerization. In these or other embodiments, the polymerization may be initiated by any free radical initiators that can produce a living polymer. Examples of initiators include reversible addition fragmentation chain transfer (RAFT), atom transfer radical polymerization (ATRP), telluride-mediated polymerization (TERP), or nitroxide mediated polymerization NMP difunctional initiators. In one or more embodiments, the photoresponsive adhesive may be polymerized through a reversible addition-fragmentation chain-transfer polymerization may be used to prepare a nanoparticle.

In one or more embodiments, vinyl monomers include those compounds with a vinyl group. Suitable vinyl monomers include, but are not limited to, acrylates, methacrylates, substituted acrylates, acrylamides, methacrylamides, and vinyl siloxanes.

Specific examples of acrylates include, but are not limited to methyl acrylate, ethyl acrylate, n-butyl acrylate, isobutyl acrylate, n-hexyl acrylate, 2-ethylhexyl acrylate, 2-carboxyethyl acrylate and hydroxybutyl acrylate.

Specific examples of methacrylates include, but are not limited to methyl methacrylate, ethyl methacrylate, n-butyl methacrylate, isobutyl methacrylate, n-hexyl methacrylate, 2-ethylhexyl methacrylate, and hydroxybutyl methacrylate.

Specific examples of acrylamides include, but are not limited to N-methyl acrylamide, N,N-dimethyl acrylamide, N-ethyl acrylamide, N,N-diethyl acrylamide, N-isopropyl acrylamide, and N-t-butyl acrylamide.

Specific examples of methacrylamides include, but are not limited to N-methyl methacrylamide, N,N-dimethyl methacrylamide, N-ethyl methacrylamide, N,N-diethyl methacrylamide, N-isopropyl methacrylamide, and N-t-butyl methacrylamide.

Specific examples of vinyl siloxanes include, but are not limited to 3-methacryloxypropyl trimethoxysilane, 3-acryloxypropyl trimethoxysilane, 3-methacryloxypropyl triethoxysilane, 3-acryloxypropyl triethoxysilane, 3-methacryloxypropyl tritert-butyloxysilane, 3-acryloxypropyl tritert-butyloxysilane, 3-methacryloxypropyl dimethoxethoxysilane, 3-acryloxypropyldimethoxethoxysilane, 3-methacryloxypropyldiethoxmethoxysilane, 3-acryloxypropyldiethoxmethoxysilane, vinyl trimethoxysilane, vinyl triethoxysilane and vinyl tris(2-methoxyethoxy)silane.

Specific examples of substituted acrylates include, but are not limited to alkyl a-hydroxymethyl acrylate and 2-hydroxyethyl acrylate. Other suitable substituted acrylates include Baylis-Hillman adducts, described in WO 2014/152850, which is incorporated by reference.

In one or more embodiments, the photoresponsive crosslinker with two acryl end groups may be defined by the formula:

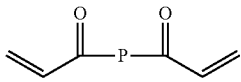

where P is a photoresponsive group.

In one or more embodiments, where photoresponsive crosslinker with two acryl end groups includes a photoresponsive that is a alkoxyphenacyl group the photoresponsive crosslinker may be defined by the formula:

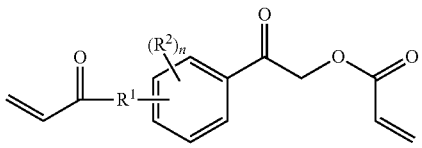

where $R^1$ is a hydrocarbon group or a substituted hydrocarbon group; each $R^2$ is a is individually a hydrogen atom, a bromine atom, an iodine atom, or an alkoxy group; and n is from 0 to 4. In these or other embodiments, where photoresponsive crosslinker with two acryl end groups includes a photoresponsive that is a alkoxyphenacyl group the photoresponsive crosslinker may be defined by the formula:

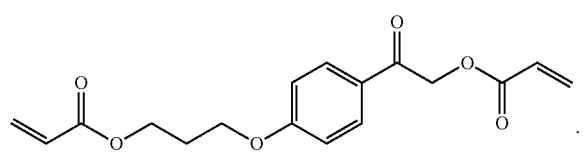 [SMILES: C=CC(=O)OCCCOc1ccc(C(=O)COC(=O)C=C)cc1]

In one or more embodiments, where photoresponsive crosslinker with two acryl end groups includes a photoresponsive that is a coumarin group the photoresponsive crosslinker may be defined by the formula:

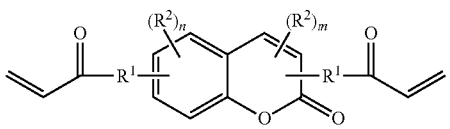

where each $R^1$ is a hydrocarbon group or a substituted hydrocarbon group; each $R^2$ is a is individually a hydrogen atom, a bromine atom, an iodine atom, or an alkoxy group; n is from 0 to 3; and m is from 0 to 1. In these or other embodiments, where photoresponsive crosslinker with two acryl end groups includes a photoresponsive that is a coumarin group the photoresponsive crosslinker may be defined by the formula:

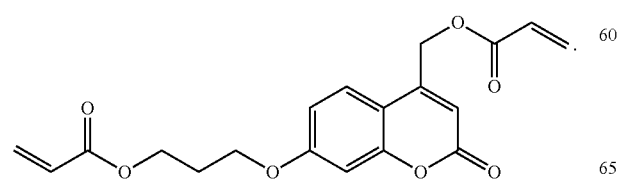

In one or more embodiments, where the pressure sensitive adhesive polymer includes a photoresponsive group that is a coumarin group the pressure sensitive adhesive polymer may include the formula

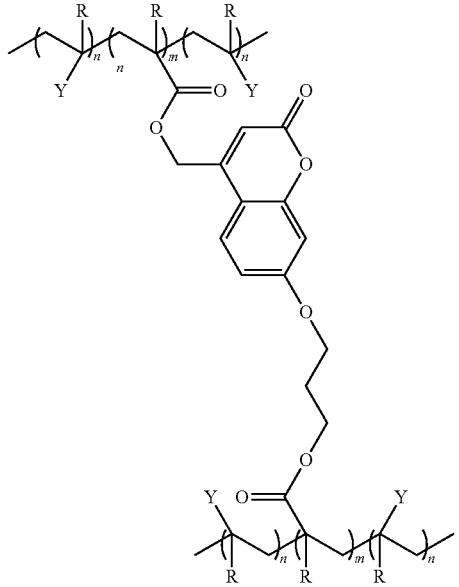

where each Y is individually an ester, amide, or siloxane group; each R is individually a hydrogen atom or an alkyl group; each n is individually 50 to 10,000 units; and each m is individually 1 to 1,000 units.

In one or more embodiments, where the pressure sensitive adhesive polymer includes a photoresponsive group that is a alkoxyphencyl group the pressure sensitive adhesive polymer may include the formula

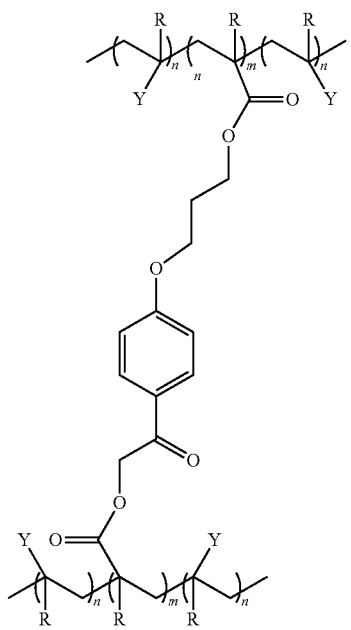

where each Y is individually an ester, amide, or siloxane group; each R is individually a hydrogen atom or an alkyl group; each n is individually 50 to 10,000 units; and each m is individually 1 to 1,000 units.

In one or more embodiments, the photoresponsive adhesive may be prepared as an aqueous dispersion type emulsion adhesive. In these or other embodiments, an aqueous dispersion type emulsion adhesive may be prepared by polymerizing a vinyl monomer and photoresponsive crosslinker with two acryl end groups together with an emulsifier in aqueous medium.

In one or more embodiments, the photoresponsive adhesive may have a backbone that includes a photoresponsive group. In these or other embodiments, the photoresponsive adhesive may be prepared with a difunctional initiation compound that includes a photoresponsive group. A difunctional initiator compound that includes a photoresponsive group has two polymerization initiation sites tethered by a bond or an organic group to a photoresponsive group. Advantageously, the difunctional initiator compound that includes a photoresponsive group imparts a photoresponsive group into the backbone of the polymer. Each initiation site is able to initiate a living polymerization. Examples of difunctional initiator compounds that include a photoresponsive group include reversible addition fragmentation chain transfer (RAFT), atom transfer radical polymerization (ATRP), telluride-mediated polymerization (TERP), or nitroxide mediated polymerization NMP difunctional initiators.

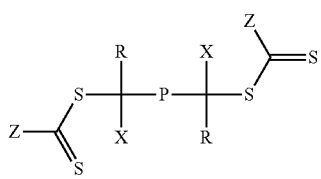

where P is a photoresponsive group; each R is individually a hydrogen atom or an alkyl group; each X is an electron withdrawing group; and each Z is a group that control C=S bond reactivity. In one or more embodiments, R and X function to stabilize the radical formed during polymerization. In one or more embodiments, the photoresponsive group may be a coumarin group. In other embodiments, the photoresponsive group may be an alkoxyphencyl group.

In one or more embodiments, the photoresponsive adhesive may be prepared as solvent-type adhesive. In these or other embodiments, the photoresponsive adhesive may be prepared polymerizing a vinyl monomer and photoresponsive crosslinker with two acryl end groups in a solution polymerization. In one or more embodiments, a solvent-type adhesive may be prepared by polymerizing a vinyl monomer and photoresponsive crosslinker with two acryl end groups together with a difunctional initiator compound that includes a photoresponsive group in a solution polymerization.

In one or more embodiments, where a difunctional RAFT agent that includes a coumarin group is used to prepare an adhesive with a polymer backbone that includes a coumarin group the adhesive with a polymer backbone that includes a coumarin group may be defined by the formula

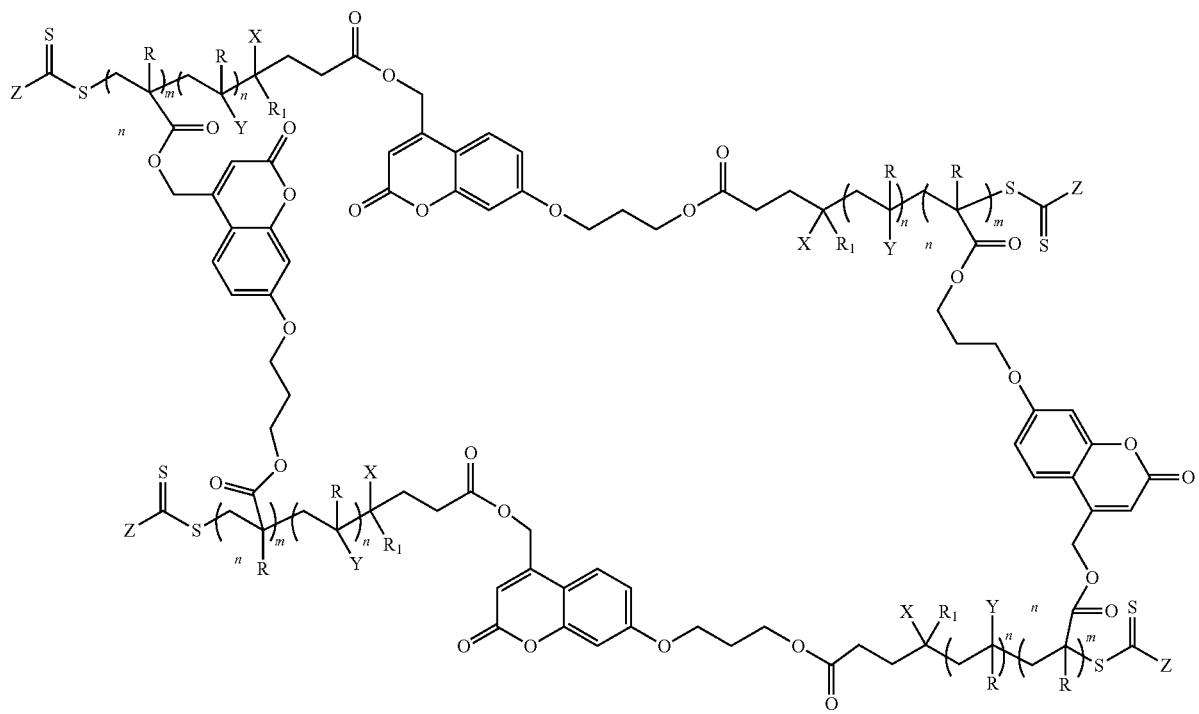

In certain embodiments, where the difunctional initiator compound that includes a photoresponsive group is a RAFT agent, the difunctional initiator compound may defined by the formula where each Y is individually an ester, amide, or siloxane group; each R is individually a hydrogen atom or an alkyl group; each n is 50 to 10,000 units; and each m is individually 1 to 1,000 units; X is individually a leaving group; each $R_1$ is individually an electron withdrawing group and each Z is a group that control C=S bond reactivity.

In one or more embodiments, where a difunctional RAFT agent that includes a alkoxyphencyl group is used to prepare a photoresponsive adhesive with a polymer backbone that includes a alkoxyphencyl group the photoresponsive adhesive with a polymer backbone that includes a alkoxyphencyl group may be defined by the formula

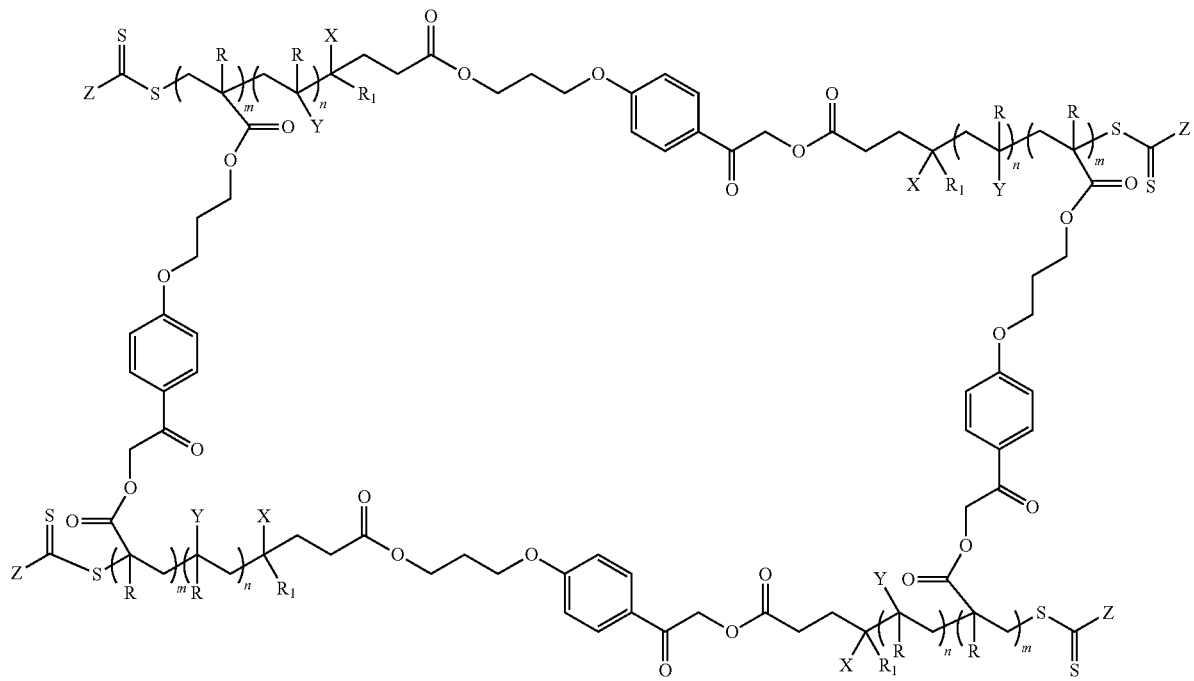

where each Y is individually an ester, amide, or siloxane group; each R is individually a hydrogen atom or an alkyl group; each n is 50 to 10,000 units; and each m is individually 1 to 1,000 units; X is individually a leaving group; each $R_1$ is individually an electron withdrawing group; and each Z is a group that control C=S bond reactivity.

In one or more embodiments, a coupling agent may be attached to the photoresponsive adhesive to increase the molecular weight and change the physical properties of the material. This will advantageously allow for hybrid class of adhesives. In one or more embodiments, the resultant polymer from a photoresponsive adhesive prepared through a RAFT polymerization includes RAFT head groups, which may be removed to produce a free polar thiol group, and the free polar thiol group is then modified by attaching to other polymers such as elastomers and PU.

In one or more embodiments, a supramolecular coupling agent may be attached to the photoresponsive adhesive to increase the molecular weight without increasing the crosslink density. This will advantageously allow for higher molecular weight without increasing the polymer chain length or crosslink density. In one or more embodiments, the resultant polymer from a photoresponsive adhesive prepared through a RAFT polymerization includes RAFT head groups, which may be removed to produce a free polar thiol group, and the free polar thiol group is then modified by attaching a supramolecular coupling agent. In one or more embodiments, the supramolecular coupling agent may be attached to the free polar thiol group by a thiol-ene click reaction.

In one or more embodiments, the supramolecular coupling agent may have a molecular weight of at least 100 Dalton in other embodiments at least 1000 Dalton, and in still other embodiments at least 10,000 Da. In one or more embodiments, the supramolecular coupling agent may be a group that is capable of forming strong hydrogen bonds. An exemplary supramolecular coupling agent is ureido-pyrimidinone (UPy).

In one or more embodiment, the photoresponsive adhesive may be a hot melt adhesive. Hot melt adhesive possesses the reversible properties of strong cohesive strength at ambient temperature and desirable melt viscosity at elevated temperatures. In one or more embodiments, a photoresponsive adhesive with a supramolecular coupling agent may be used as a hot melt adhesive.

In one or more embodiments, where ureido-pyrimidinone is used as a supramolecular coupling agent on a photoresponsive adhesive prepared with a difunctional RAFT agent that includes a coumarin group the photoresponsive adhesive with a polymer backbone that includes a coumarin group may be defined by the formula

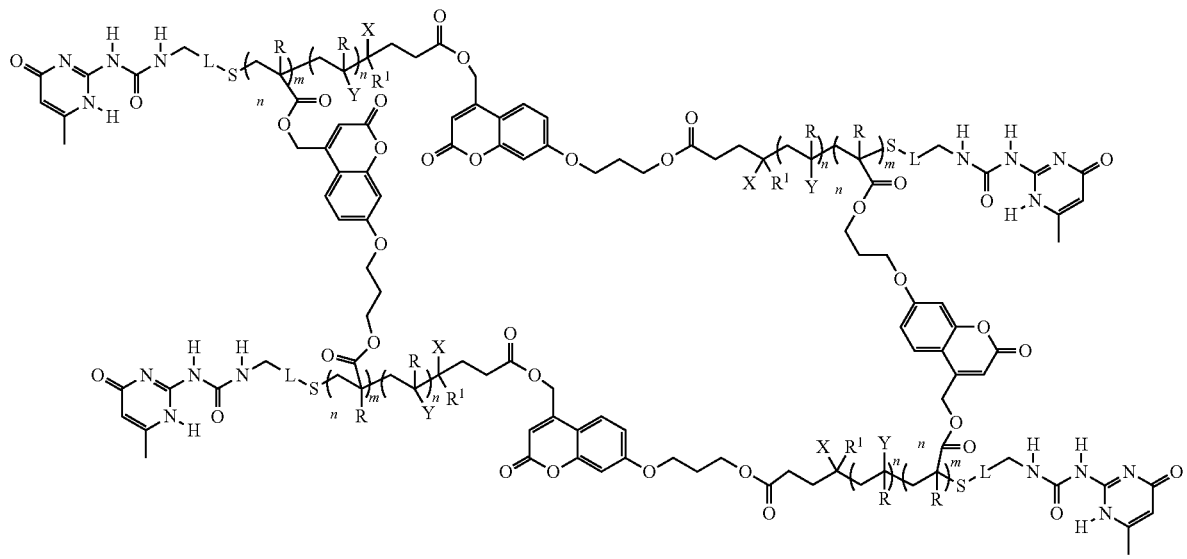

where each Y is individually an ester, aminde, or siloxy group; each R is individually a hydrogen atom or an alkyl group; each n is 50 to 10,000 units; and each m is individually 1 to 1,000 units; X is individually a leaving group; each $R_1$ is individually an electron withdrawing group; L is a hydrocarbon group; and each Z is a group that control C=S bond reactivity.

In one or more embodiments, where ureido-pyrimidinone is used as a supramolecular coupling agent on a photoresponsive adhesive prepared with a difunctional RAFT agent that includes a alkoxyphencyl group the photoresponsive adhesive with a polymer backbone that includes a alkoxyphencyl group may be defined by the formula The photoresponsive adhesives may be applied to a variety of substrates, including paper, cardboard, wood, glass, and metal. Due to photoresponsive nature of the photoresponsive adhesives, the photoresponsive adhesive may be applied to transparent or partially transparent substrate. The transparent or partially transparent substrate may be completely transparent or transparent to at least one wavelength that allows the photoresponsive group to alter the strength properties of the photoresponsive adhesive. In one or more embodiments, a photoresponsive adhesive in a

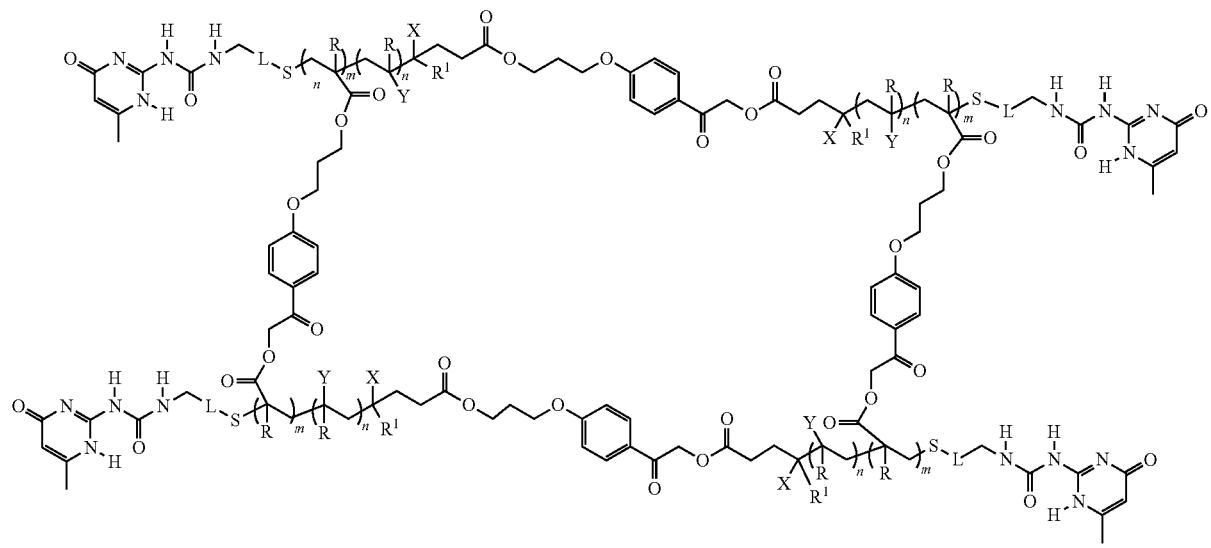

where each Y is individually an ester, aminde, or siloxy group; each R is individually a hydrogen atom or an alkyl group; each n is 50 to 10,000 units; and each m is individually 1 to 1,000 units; X is individually a leaving group; each high strength conformation may be used to attach a transparent or partially transparent substrate to a surface. Advantageously, the transparent or partially transparent substrate allows for light to pass to the photoresponsive adhesive to switch the photoresponsive adhesive to a low strength conformation, allowing the substrate to be removed from the surface easily. In these or other embodiments, a removable light occlusive layer may be attached to the transparent or partially transparent substrate to prevent the photoresponsive adhesive from prematurely switching to a low strength conformation.

In one or more embodiments, the photoresponsive adhesive may be used as an adhesive in a medical dressing. Medical dressings are described in U.S/ Pat. Pub. 2013/0017246, which is incorporated herein. In one or more embodiments, a medical dressing may comprise a transparent or partially transparent backing layer with a first and a second side; and a pressure sensitive adhesive polymer comprising crosslinked adhesive polymers with a cross-linker that includes a photoresponsive group coasted on the first side of the backing layer. In these or other embodiments, the medical dressing may include a removable light occlusive layer attached to the second side of the transparent or partially transparent backing layer.

While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

Examples

Synthesis of 2-hydroxy-1-(4-(3-hydroxypropoxy) phenyl) ethan-1-one (Alkoxyphenacyl Moiety)

In a 500 ml round bottom flash equipped with a magnetic stir bar, 1-(4-(3-hydroxypropoxy)phenyl)ethan-1-one (4.0 g, 20.6 mmol), [bis(trifluoroacetoxy)iodo]benzene (13.28 g, 30.9 mmol), trifluoroacetic acid (1.58 ml, 20.6 mmol), acetonitrile (82.4 ml, 20.6 mmol) and water (16.5 ml, 20.6 mmol) were added. The reaction was carried out at 45° C. for 24 hours. After that, the acetonitrile and trifluoroacetic acid were removed under reduced pressure. The residue was extracted by ethyl acetate for three times. Then the solvent was removed under reduced pressure and the compound was purified by column chromatography to give a white solid. (2.62 g, 60%)

$^1$H NMR (300 MHz, CHLOROFORM-d) ppm 2.08; (quin, J=6.00 Hz, 2H) 3.55; (br. s., 1H) 3.88; (t, J=6.00 Hz, 2H) 4.21; (t, J=6.15 Hz, 2H) 4.77-4.87; (m, 2H) 6.98; (m, J=8.78 Hz, 2H) 7.13-7.51; (m, 1H) 7.26; (s, 1H) 7.89; (m, J=8.78 Hz, 2H)

Synthesis of Alkoxyphenacyl-Based Diacrylate Crosslinker

In a 100 ml round-bottom flask equipped with a magnetic stir bar, Alkoxyphenacyl monomer (2.1 g, 10.0 mmol) was dissolved in anhydrous dichloromethane (30 ml). Triethylamine (4.18 ml, 30.0 mmol) was added and the solution was cooled in ice bath for 0.5 hour. Acryloyl chloride (3.29 ml, 40.0 mmol) was added slowly by a syringe pump under stirring. The reaction was carried out at room temperature overnight. After that, the insoluble by-product of triethylamine chloride was removed by filtration and the filtrate was washed with brine solution and deionized water and dried over anhydrous $Na_2SO_4$. Then the solution was concentrated under reduced pressure and the compound was purified by column chromatography to give a white solid (0.99 g, 31%).

$^1$H NMR (300 MHz, CHLOROFORM-d) ppm 2.20; (quin, J=6.22 Hz, 2H) 4.14; (t, J=6.15 Hz, 2H) 4.37; (t, J=6.29 Hz, 2H) 5.39; (s, 2H) 5.79-6.00; (m, 2H) 6.06-6.35; (m, 2H) 6.37-6.62; (m, 2H) 6.86-7.03; (m, 2H) 7.82-7.99; (m, 2H)

Synthesis of 4-(hydroxymethyl)-7-(3-hydroxy-propoxy)-2H-chromen-2-one (Coumarin Moiety)

In a 50 ml round-bottom flask equipped with a magnetic stir bar, 7-hydroxy-4-(hydroxymethyl)-2H-chromen-2-one (1.0 g, 5.2 mmol), 18-crown-6 (0.7 g, 2.6 mmol), potassium carbonate (2.0 g, 14.5 mmol) were added. The flask was evacuated and refilled with nitrogen for three times. Then anhydrous acetone (15 ml) was added and the solution was stirred for 30 min. After that, 3-bromopopan-1-ol (0.96 ml, 10.8 mmol) was added and the reaction was refluxed for 24 hours. The reaction solution was filtered and the filtrate was washed by acetone for 3 times. Then the filtrate was concentrated under reduced pressure and the product was purified by column chromatography to give a yellow solid (1.07 g, 82%).

$^1$H NMR (300 MHz, DMSO-$d_6$) ppm 1.88; (t, J=6.29 Hz, 2H) 3.56; (q, J=5.85 Hz, 2H) 4.15; (t, J=6.29 Hz, 2H) 4.56; (t, J=5.12 Hz, 1H) 4.72; (d, J=4.68 Hz, 2H) 5.59; (t, J=5.56 Hz, 1H) 6.29; (s, 1H) 6.87-7.04; (m, 2H) 7.61; (d, J=8.78 Hz, 1H)

Synthesis of Coumarin-Based Crosslinker

In a 100 ml round-bottom flask equipped with a magnetic stir bar, Coumarin monomer (2.0 g, 8.0 mmol) was dissolved in anhydrous dichloromethane (20 ml). Triethylamine (2.78 ml, 20.0 mmol) was added and the solution was cooled in ice bath for 0.5 hour. Acryloyl chloride (2.58 ml, 32.0 mmol) was added slowly by a syringe pump. The reaction was carried out at room temperature overnight. After that, the insoluble by-product of triethylamine chloride was removed by filtration and the filtrate was washed with brine solution and deionized water and dried over anhydrous $Na_2SO_4$. The solution was concentrated under reduced pressure and the product was purified by column chromatography to give a yellow solid (0.97 g, 34%).

$^1$H NMR (300 MHz, CHLOROFORM-d) ppm 2.15-2.29; (m, 2H) 4.14; (t, J=6.15 Hz, 2H) 4.38; (t, J=6.29 Hz, 2H) 5.36; (d, J=1.17 Hz, 2H) 5.86; (dd, J=10.25, 1.46 Hz, 1H) 5.99; (dd, J=10.25, 1.17 Hz, 1H) 6.07-6.19; (m, 1H) 6.19-6.31; (m, 1H) 6.36; (s, 1H) 6.43; (dd, J=17.27, 1.46 Hz, 1H) 6.55; (dd, J=17.27, 1.17 Hz, 1H) 6.77-6.96; (m, 2H) 7.43; (d, J=8.49 Hz, 1H)

Emulsion Polymerization with Alkoxyphenacyl-Based Photoresponsive Crosslinker

Polymers with different amount of cross-linker (0.1%, 0.2%, 0.3% and 0.5% mole fraction) were synthesized to obtain the optimal polymer properties. As an example, the synthesis of polymers with 0.5% cross-linker is as follows: in a 50 ml round-bottom flask equipped with a magnetic stir bar, water (6 ml) and sodium dodecyl sulfate (16.2 mg) were added. A mixture of butyl acrylate (1.86 g, 14.5 mmol, 89.5%), 2-caboxyethyl acrylate (0.23 g, 1.6 mmol, 10%) and alkoxyphenacyl-based cross-linker (25.8 mg, 0.081 mmol, 0.5%) was added dropwise. Then a stock solution (1 ml) of 4,4'-azobis(4-cyanovaleric acid) (3.4 mg) and sodium bicarbonate (3.6 mg) was added. After degassing for 30 minutes, the reaction was carried out at 70° C. for 10 hours.

Emulsion Polymerization with Coumarin-Based Photoresponsive Crosslinker

Polymers with different amount of cross-linker (0.1%, 0.2%, 0.3% and 0.5% mole fraction) were synthesized to obtain the optimal polymer properties. As an example, the synthesis of polymers with 0.5% cross-linker is as follows: in a 50 ml round-bottom flask equipped with a magnetic stir bar, water (6 ml) and sodium dodecyl sulfate (16.2 mg) were added. A mixture of butyl acrylate (1.86 g, 14.5 mmol, 89.5%), 2-caboxyethyl acrylate (0.23 g, 1.6 mmol, 10%) and coumarin-based cross-linker (29.0 mg, 0.081 mmol, 0.5%) was added dropwise. Then a stock solution (1 mL) of 4,4'-azobis(4-cyanovaleric acid) (3.4 mg) and sodium bicarbonate (3.6 mg) was added. After degassing for 30 minutes, the reaction was carried out at 70° C. for 6 hours.

Characterization of Emulsion

Typical characterization techniques of the emulsions are Dynamic Light Scattering (DLS) for particle size, solid content, and monomer conversion. The particle size of each emulsion was measured by using Dynamic Light Scattering. Monomer conversion was assured by nuclear magnetic resonance (NMR). And the solid content was determined by measurement of weight before and after the drying process at room temperature for 24 h in vacuum oven.

Solid content(wt %)=(W2/W1)*100% where W2 is the weight of dried polymer after vacuum drying and W1 is the weight of the emulsion before vacuum drying.

Characterization of Photo-Switchable Performance

As mentioned before, the typical characterizations of PSAs are tack, peel and shear strength. In this project, peel test was chose to characterize the adhesion property, whereas the lap shear test was used to evaluate the cohesion strength.

Sample Preparation

The emulsion sample was prepared onto quartz plates, which is UV transmissible so that the irradiation test can be measured. Quartz plates were put on to a horizontal desk and pipetted with 150 μl emulsion on the fix area (25 mm*20 mm). The emulsion was spread to form a homogeneous emulsion film and then dry at room temperature for 24 h. After the sample is dry, the sample was vacuumed in vacuum oven at 37° C. for 2 h to remove the water thoroughly. Thickness of these samples varies from 85-96 μm and they are further used for peel test and lap shear.

Lap Shear and Peel Test

Lap shear and peel test were both measured on the TA. XT Plus texture analyser. For the experiments of each emulsion-based PSAs, either for peel or shear test, ten samples were prepared based on different test standard. Five samples of them were tested without irradiation and the other five left were first irradiated for 5 minutes and then continue for specific testing. The irradiation experiments were conducted by a Rayonet reactor at 300 nm (16 tubes, 5.34 mW/cm2).

For the lap shear of each emulsion, the ten dry samples are covered with another quartz plate and clamped for 45 min, respectively. Then the clamps were removed. Five samples were placed under irradiation for 5 min and the other five were not. And the shear rate used was 5 mm/s at room temperature.

For the 180° peel test, the peel strength of PSAs was measured at a peel rate of 25 mm/s. A 25 mm wide PE film (UVO treated) was adhered to the dry sample with FINAT roller pressure. The peel test sample was irradiated for 5 min. After 2 min dwell, the peel of the PET film was performed. And the other samples without irradiation were tested in the same procedures except the irradiation step.

Lap shear was carried out for 0.1%, 0.2% and 0.3% of crosslinker and it was found that about 65% of the adhesive strength was lost for the 0.3% sample. Therefore peel test was carried out for the same sample to find that about 70% of the peel strength was lost after exposure to light.

| Lap shear Data | |
|---|---|
| Without irradiation | 100% strength |
| With irradiation | |
| 0.1% crosslinker | 95% strength remains |
| 0.2% crosslinker | 70% strength remains |
| 0.3% crosslinker | 35% strength remians |
| Peel Test Data | |
| Without irradiation | 100% strength |
| 0.3% crosslinker | 30% strength remains |

Lap Shear data and B.) Peel Test data.

As seen from the data, there is significant decrease in the peel strength for a sample containing 0.3% of our novel crosslinker. This can be thus used in a medical bandage application wherein atraumatic removal of wound dressings is a strong need.

The invention claimed is:

1. A photoresponsive adhesive polymer comprising adhesive polymers crosslinked with a crosslinker that includes a photoresponsive group not pendantly attached to the crosslinker, where the photoresponsive adhesive polymer is prepared by polymerizing a vinyl monomer and photoresponsive crosslinker defined by the formula:

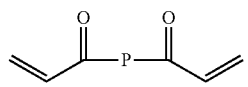

where P is an alkoxyphenacyl photoresponsive group, where the adhesive polymers are polysiloxanes, and wherein the alkoxyphenacyl photoresponsive group has the following formula:

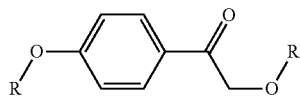

where each R is individually an organic group.

2. A photoresponsive adhesive polymer having the formula

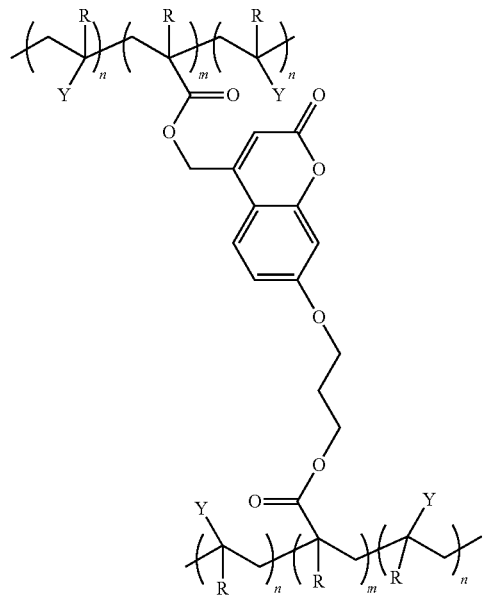

where each Y is individually an ester, amide, or siloxane group; each R is individually a hydrogen atom or an alkyl group; each n is individually 50 to 10,000 units; and each m is individually 1 to 1,000 units.

3. The photoresponsive adhesive polymer of claim 1, where the photoresponsive adhesive polymer includes the formula

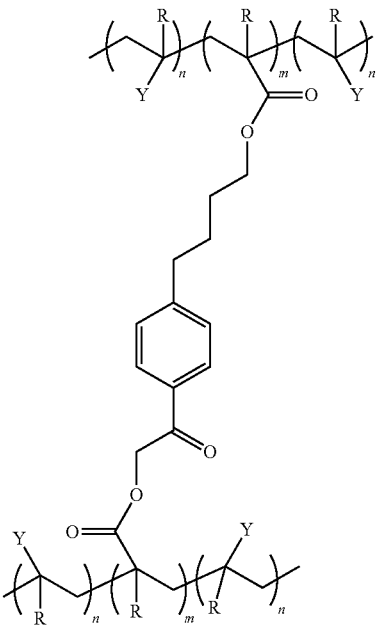

where each Y is individually an ester, amide, or siloxane group; each R is individually a hydrogen atom or an alkyl group; each n is individually 50 to 10,000 units; and each m is individually 1 to 1,000 units.

4. The photoresponsive adhesive polymer of claim 2, where the adhesive polymers have a backbone that includes a photoresponsive group.

5. The photoresponsive adhesive polymer of claim 4, where the photoresponsive adhesive polymer is defined by the formula

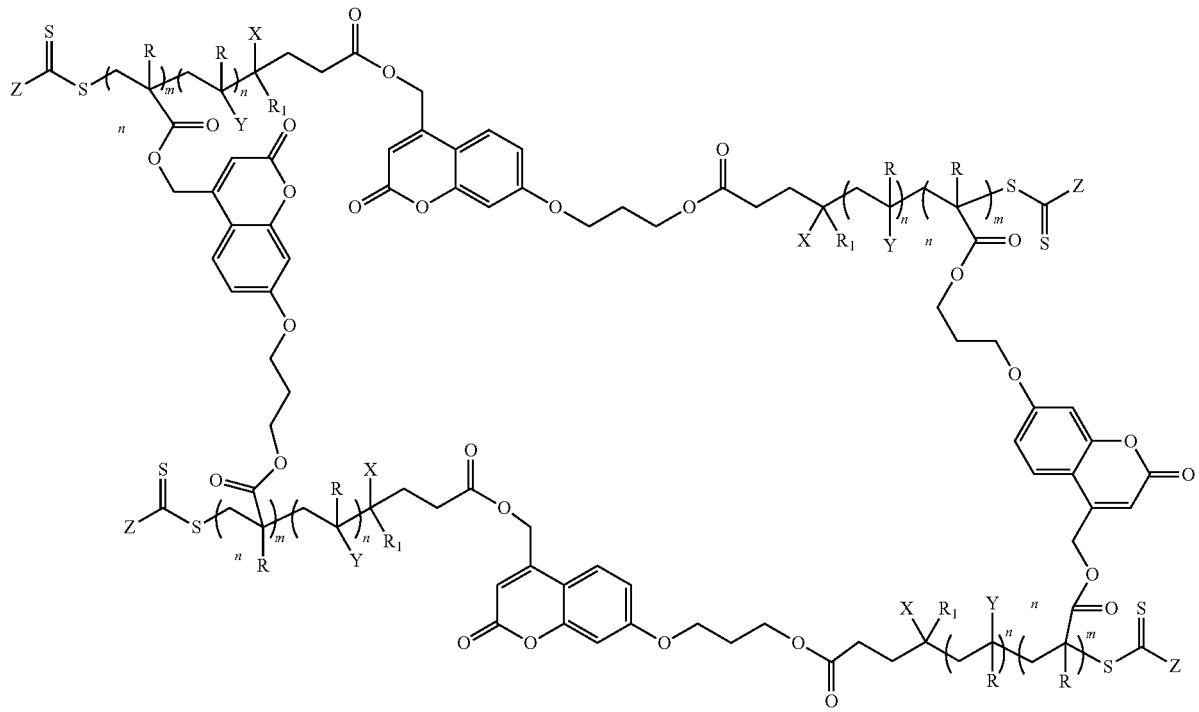

where each Y is individually an ester, amide, or siloxane group; each R is individually a hydrogen atom or an alkyl group; each n is 50 to 10,000 units; and each m is individually 1 to 1,000 units; X is individually a leaving group; each $R_1$ is individually an electron withdrawing group; and each Z is a group that control C=S bond reactivity.

6. The photoresponsive adhesive polymer of claim 1, where the photoresponsive adhesive polymer includes the formula

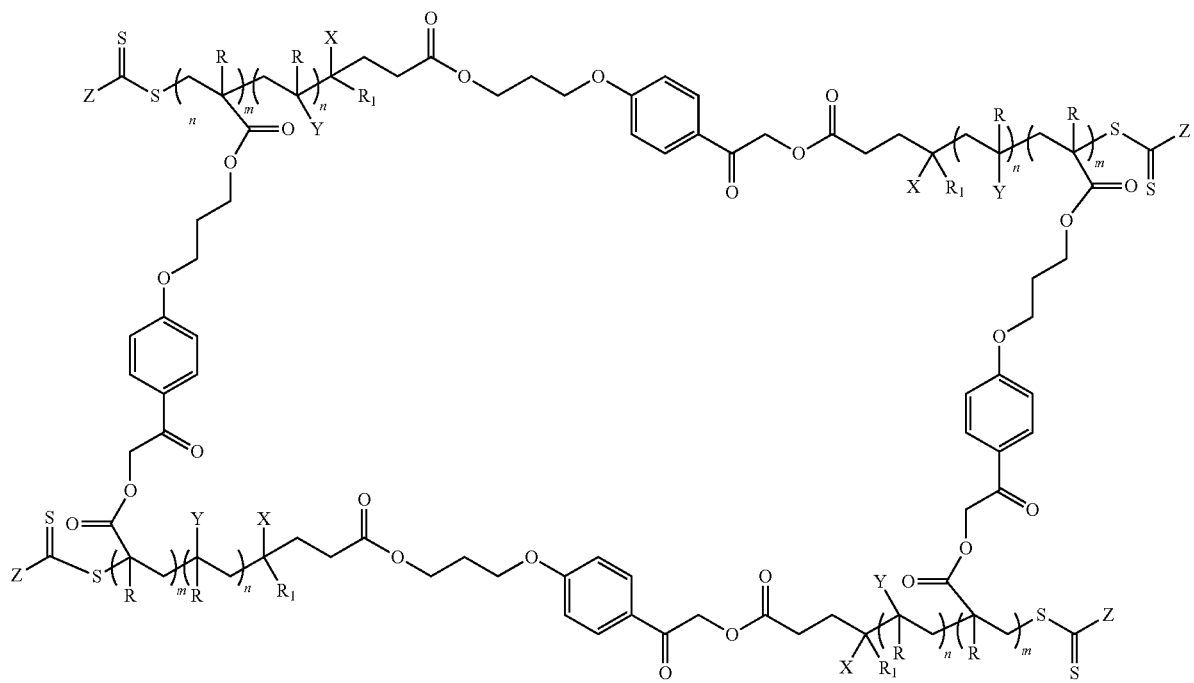

where each Y is individually an ester, amide, or siloxane group; each R is individually a hydrogen atom or an alkyl group; each n is 50 to 10,000 units; and each m is individually 1 to 1,000 units; X is individually a leaving group; each $R_1$ is individually an electron withdrawing group; and each Z is a group that control C=S bond reactivity.

7. The photoresponsive adhesive polymer of claim 1, where the photoresponsive adhesive polymer has a high adhesive strength conformation and a low adhesive strength conformation, and the high strength conformation is at least 2 times stronger than the low strength conformation.

8. A photoresponsive adhesive polymer comprising adhesive polymers crosslinked with a crosslinker that includes a photoresponsive group not pendantly attached to the crosslinker, where the photoresponsive adhesive polymer includes the formula

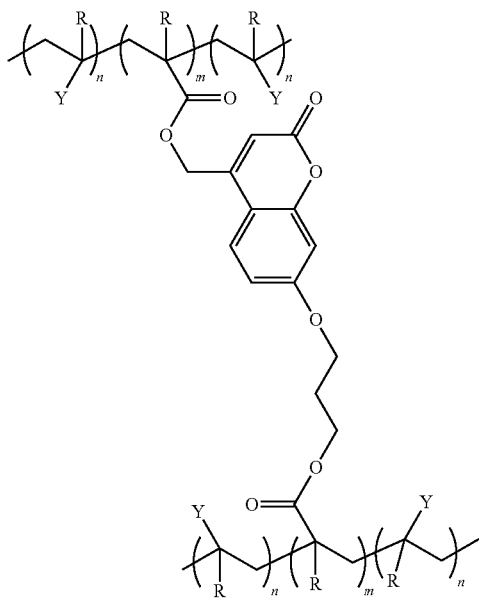

where each Y is individually an ester, amide, or siloxane group; each R is individually a hydrogen atom or an alkyl group; each n is individually 50 to 10,000 units; and each m is individually 1 to 1,000 units.

9. A photoresponsive adhesive polymer comprising adhesive polymers crosslinked with a crosslinker that includes a photoresponsive group not pendantly attached to the cross linker, where the photoresponsive adhesive polymer includes the formula

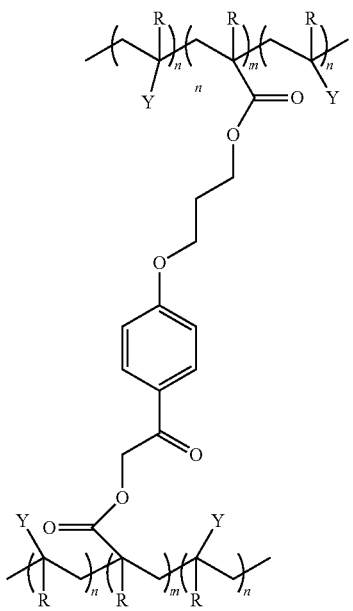

where each Y is individually an ester, amide, or siloxane group; each R is individually a hydrogen atom or an alkyl group; each n is individually 50 to 10,000 units; and each m is individually 1 to 1,000 units.

* * * * *